United States Patent [19]

Elderton

[11] 4,417,474
[45] Nov. 29, 1983

[54] DENSITOMETER

[75] Inventor: Peter P. Elderton, Fountain Valley, Calif.

[73] Assignee: ITT, New York, N.Y.

[21] Appl. No.: 218,662

[22] Filed: Dec. 22, 1980

[51] Int. Cl.³ ............................................. G01N 9/26
[52] U.S. Cl. ................................................... 73/438
[58] Field of Search .................................... 73/438

[56] References Cited

U.S. PATENT DOCUMENTS 2,287,027  6/1942  Cummins, Jr. ......................... 73/438
3,175,403  3/1965  Nelson ................................... 73/438
3,481,203  12/1969  Ackerman et al. .................... 73/438

Primary Examiner—Donald O. Woodiel
Attorney, Agent, or Firm—T. E. Kristofferson; A. D. Stolzy; T. L. Peterson

[57] ABSTRACT

A densitometer for use by itself or in a net oil computer. The densitometer includes two differential pressure units to detect the difference in pressure between two corresponding pairs of points and the differences substracted to provide a corrected density output signal. This output signal is then essentially independent of viscosity and/or other variables.

13 Claims, 4 Drawing Figures

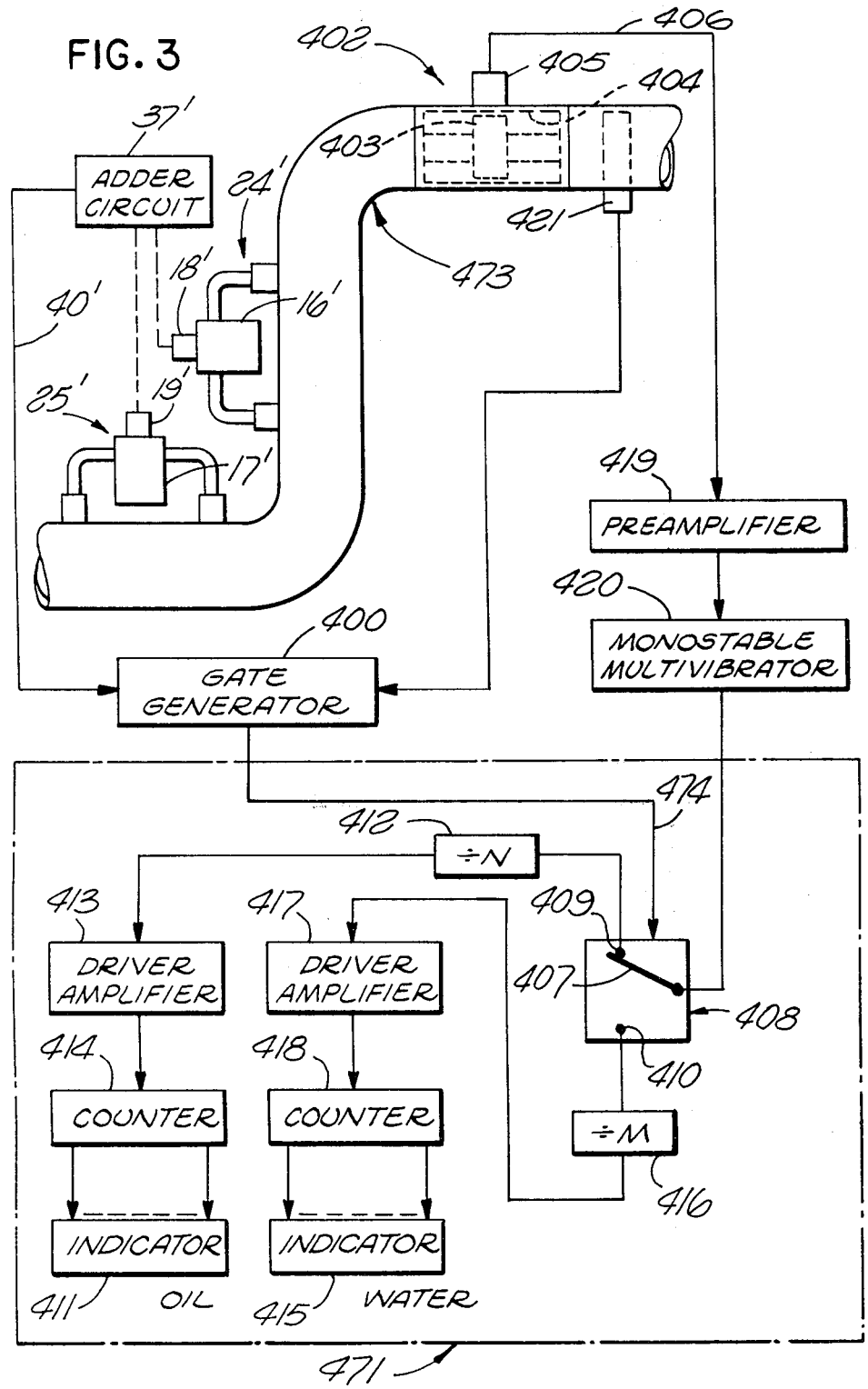

DENSITOMETER

BACKGROUND OF THE INVENTION

This invention relates to fluid sensing instruments, and more particularly to a densitometer or the like.

PRIOR ART STATEMENT

A number of U.S. patents have issued that disclose net oil computers. See Elderton U.S. Pat. No. 4,059,744 issued Nov. 22, 1977, and the references cited therein. The Elderton patent discloses a differential pressure unit (DPU) in a net oil computer. For example, see DPU 472 in FIG. 1.

SUMMARY OF THE INVENTION

In accordance with the system of the present invention, a densitometer is provided having one or two differential pressure units, and utilization means connected from at least one of the differential pressure units.

BRIEF DESCRIPTION OF THE DRAWINGS

In the accompanying drawings which illustrate exemplary embodiments of the present invention:

FIG. 3 is a diagrammatic view of an alternative embodiment of the invention.

DESCRIPTION OF THE PREFERRED EMBODIMENT

Figure 1:
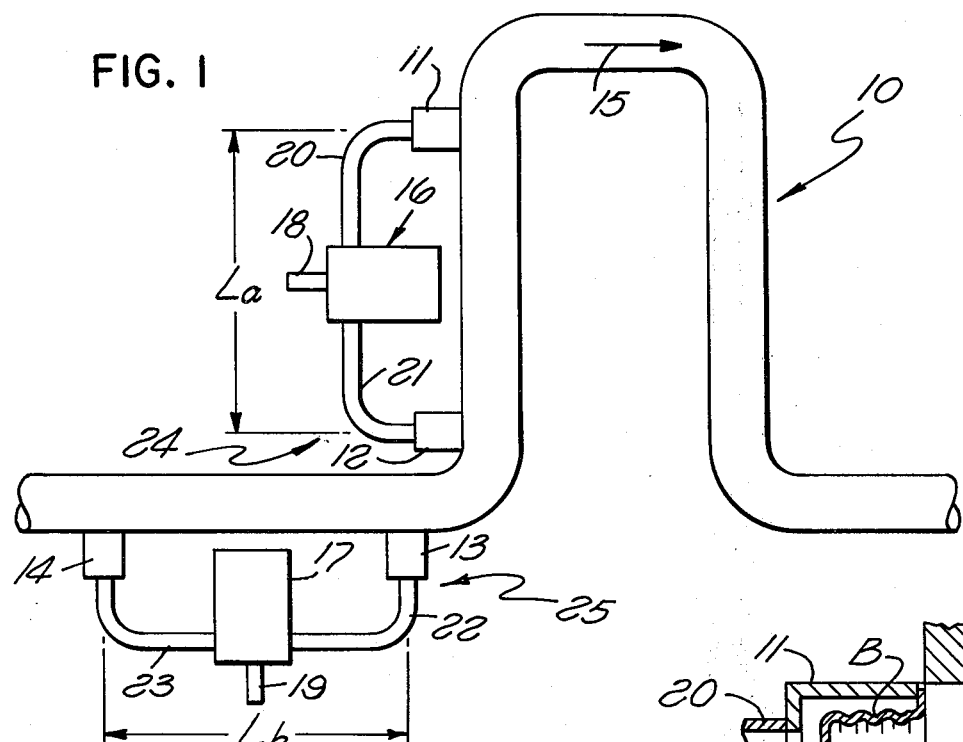
FIG. 1 is a diagrammatic view of a portion of the embodiment of the densitometer of the present invention.

In FIG. 1, a portion of the apparatus of the invention is shown mounted to a pipeline 10 carrying, for example, a mixture of oil and water. Flow is in the direction of arrow 15 but may be in the opposite direction in certain cases.

Arrangements are provided at 24 and 25. Arrangement 24 includes a vertically spaced pair of bellows housings 11 and 12. A horizontally spaced pair of bellows housings 13 and 14 are also provided. Differential pressure units (DPUs) 16 and 17, rotate output shafts 18 and 19 in proportion to the difference in the pressures of the fill fluid in tubing at 20, 21 and 22, 23, respectively. The arrangement 24 may be identical to that of 25, if desired. Also, length $L_a$ may be equal to length $L_b$. The operation of arrangement 24 may be identical to an arrangement shown in said patent.

Figure 2:
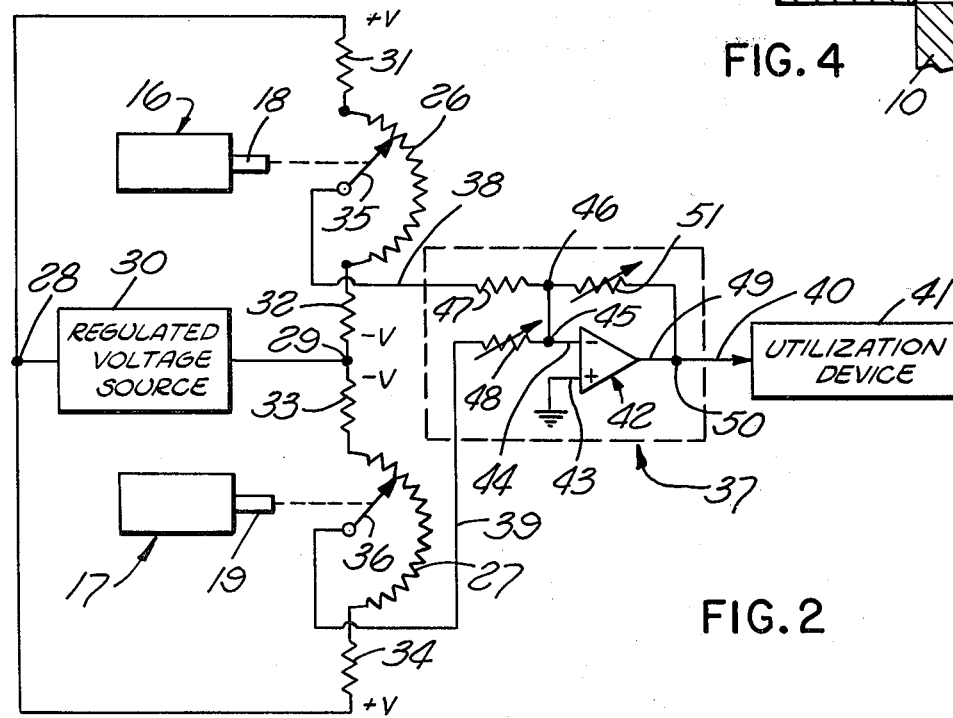
FIG. 2 is a diagrammatic view of the remainder of the embodiment shown in FIG. 1.

The outputs of DPUs 16 and 17 are taken as shown in FIG. 2. Potentiometer windings are provided at 26 and 27. Parallel circuits are provided between output junctions 28 and 29 of a regulated voltage source 30. One circuit includes a resistor 31, winding 26 and a resistor 32. The other circuit includes a resistor 33, winding 27 and a resistor 34.

Shafts 18 and 19 operate potentiometer wipers 35 and 36. A conventional analog adder is provided at 37 connected from wipers 35 and 36 via leads 38 and 39 to an input lead 40 of a utilization device 41. Utilization device 41 may be a voltmeter calibrated in density or specific gravity, another indicator or a circuit to read in net oil and/or net water or any other device.

The signal on lead 38 may be directly proportional to $d_t$ where $$d_t = d_a + d_b \quad (1)$$

$d_a$ is the true density of the fluid in pipeline 10, and $d_b$ is a density correction as a function of a fluid variable such as, for example, viscosity.

The signal on lead 39 is thus of a polarity opposite that of the signal on lead 38 and proportional to $-d_b$.

The signal appearing on lead 40 is then directly proportional to $d_a$.

$$d_a = d_t + (-d_b) \quad (2)$$

In accordance with the present invention, the addition of $(-d_b)$ or the subtraction of $+d_b$ may be done by any conventional means.

Adder 37 is conventional. A differential amplifier is provided at 42 having a grounded noninverting input 43, and an inverting input 44 connected from a junction 45.

Junctions 45 and 46 are connected together. A resistor 47 is connected from lead 38 to junction 46. A resistor 48 is connected from lead 39 to junction 45. Amplifier 42 has an output 49 connected to utilization device 41 through a junction 50. A feedback resistor 51 is connected between junctions 46 and 50.

A net oil computer is shown in FIG. 3. Parts 473, 24' and 25' may be identical, if desired, to respective parts 10, 24, and 25 shown in FIGS. 1 and 2. In FIG. 3, 37' may include all of the circuits shown in FIG. 2 (26–40).

A net oil computer constructed in accordance with the present invention is shown in FIG. 3. The embodiment of FIG. 3 can produce pulses approximately or exactly proportionately to oil and/or water according to percent by weight or volume. The computer of FIG. 3 has components mounted in or on pipeline 473. As in FIGS. 1 and 2, two conventional differential pressure units 16' and 17' are provided in arrangements 24' and 25', respectively. Potentiometer arms in adder circuit 37' (not shown) are turned in proportion to differential pressure by the DPU output shafts 18' and 19', respectively. For the details of the structures shown in arrangements 24' and 24, for example, see the said patent. Bellows in housings 11, 12, 13 and 14 separate fill fluid from the oil and water mixture.

Any suitable mechanical-to-electrical device may connect shafts 18' and 19' to a gate generator 400 by a lead 40' similar to lead 40.

In FIG. 3, the net oil computer also includes a turbine flowmeter 402 which has a turbine bladed rotor 403 and a stator 404. Flowmeter 402 also has a magnetic pickup 405. Flowmeter 402 is entirely conventional and produces a pulse train on an output lead 406. The pulse repetition frequency (PRF) of the pulses on lead 406 is directly proportional to the volume flow rate within pipeline 473. In other words, the flow rate is the rate of volume flow of both oil and water combined, that is the mixture thereof. The output of flowmeter 402 is impressed on the pole 407 of a conventional electronic switch 408 in an output circuit 471. Switch 408 may, however, be a relay, other switch or otherwise. Switch 408 has contacts 409 and 410. Contact 409 is connected to a conventional indicator 411 via a conventional frequency divider 412, a conventional driver amplifier 413 and a conventional counter 414. Contact 410 is connected to a conventional indicator 415 through a conventional frequency divider 416, a conventional driver amplifier 417 and a conventional counter 418.

Flowmeter 402 is connected to switch pole 407 through a conventional preamplifier 419 and a conventional monostable multivibrator 420.

Switch 408 is operated by gate generator 400 that receives input signals from adder circuit 37' and a temperature probe 421. The turbine rotor 403 and temperature probe 421 are both immersed in the mixture of oil and water flowing in pipeline 473.

Scalers 412 and 416 may be employed to cause indicators 411 and 415 to read directly in barrels of oil and barrels of water, respectively, or in units of volume or weight thereof.

If the output pulses of gate generator 400 are positive, as described in the said patent, pole 407 will engage one of the contacts 409 and 410. That is, the engagement occurs during the width of the pulse. Conversely, during the time between pulses, pole 407 will engage the other of the contacts 409 and 410.

Everything disclosed in FIG. 3 may be identical to corresponding parts shown in the said patent except arrangement 25' and adder circuit 37', the latter two being of the described hereinbefore in connection with FIGS. 1 and 2. The said patent is hereby incorporated herein by this reference hereto.

As is conventional, variable resistors (see the said patent) are adjusted in accordance with the densities of the water and oil, respectively, in pipeline 473. The water and oil densities are obtained by taking a sample of the mixture thereof in pipeline 473, and then putting the sample through a centrifuge. The densities of the oil and water so separated are then measured. The variable resistors are then set in proportion to the respective water and oil densities measured. Various densities may be encountered due to impurities, dissolved solids and otherwise. The specific gravity of the water in pipeline 473 might typically be 1.07. The oil in pipeline 473, which may or may not be crude oil, may have a typical specific gravity of 0.85.

OPERATION

In the operation of the embodiment of the invention illustrated in FIG. 3, DPU 16' and DPU 17' in combination with adder circuit 37' delivers a voltage to gate generator 400 which is directly proportional to the true mean density $d_a$ of the mixture of oil and water flowing in pipeline 473. Gate generator 400 then produces output pulses of widths which are directly proportional to the percent, by volume, of oil flowing in pipeline 473. Temperature probe 421 supplies an input to gate generator 400 to adjust the output in accordance with changes in the temperature of the oil flowing in pipeline 473, this temperature being the same as the temperature of the mixture of oil and water flowing in pipeline 473. Switch 408 in output circuit 471 is constructed to deliver pulses to counters 414 and 418 through driver amplifiers 413 and 417, respectively, and dividers 412 and 416, respectively, so that indicators 411 and 415, respectively, will indicate the total mass or volume of oil and water, respectively, which has passed through that portion of pipeline 473 show in in FIG. 1. (For the mass or volume calculations see the said patent and the references cited therein and thereagainst).

Gate generator 400 controls the position of the pole 407 of switch 408 via lead 474 to divert, alternately, pulses received from the output of monostable multivibrator 420 connected via pole 407 to dividers 412 and 416.

The pulse width of the multivibrator pulses is much shorter than those appearing at the output of gate generator 400.

Note will be taken that the water in pipeline 473 will not normally be pure and may contain sodium chloride and/or other contaminants in or out of solution.

Figure 4:
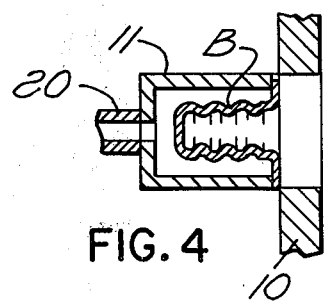
FIG. 4 is a broken away vertical sectional view of a portion of FIG. 1.

In FIG. 4, tubing 20, housing 11, pipeline 10 and a bellows B or any other arrangement, may be employed with identical and related parts for 12, 21, 13, 22, 14 and 23 shown in FIG. 1.

If pressures of $p_a$, $p_b$, $p_c$ and $p_d$ appear in pipeline 10 at 11, 12, 13 and 14, respectively, the DPU shaft 18 turns in direct proportion to $(p_a-p_b)$ and DPU shaft 19 turns in direct proportion to $(p_c-p_d)$. Over length $L_b$, the interior of pipeline 10 is identical to that portion thereof over length $L_a$. The pressure head loss due to friction in each length $L_a$ and $L_b$ is thus the same. The true mean density $d_a$ then is $$d_a = K_a(p_a-p_b) - K_b(p_c-p_d) \quad (3)$$

where $K_a$ and $K_b$ are negative constants, and $$K_a = \frac{1}{L_a}, \quad (4)$$

Density equals pressure divided by height. $K_b$ will normally have the dimension of the reciprocal of length $L^{-1}$. The term $K_b(p_c-p)$ may thus represent pressure head loss times $d_a$ due to pipeline friction and/or viscosity and/or changes in viscosity.

From equations (2) and (3), $$d_t = K_a(p_a-p_b) \quad (5)$$

$$d_b = K_b(p_c-p_d) \quad (6)$$

If desired, $K_a$ and $K_b$ may be derived empirically by using typical oil and water densities and typical proportions thereof.

It is well known that the feet head lost in pipe friction is as follows:

$$h' = \frac{fLv^2}{2gd} \quad (7)$$

where
f is the coefficient of friction,
L is the length of the pipe in feet,
v is the velocity of the flow in feet per second,
g is 32.2 feet per second per second, and
d is the inside diameter of the pipe in inches.

It is known that sometimes the term f may be alternatively expressed as one of two functions $f_a$ and $f_b$ of viscosity Z, v and specific gravity S as follows:

$$f_a = 0.00181 + 0.00662 \left(\frac{Z}{DvS}\right)^{0.355} \quad (8)$$

$$f_b = 0.0035 + 0.00594 \left(\frac{Z}{DvS}\right)^{0.424} \quad (9)$$

where $D = 12d$.

Other more sophisticated methods of computation may, of course, be used if desired.

The formulas (8) and (9) are based upon turbulent flow, as opposed to viscous flow. All ordinary pure water velocities are involved with turbulent flow.

Note that equation (3) may be mechanized another way:

$$d_a = K_a(p_a - p_c) - K_b(p_d - p_b) \tag{10}$$

Note will be taken that the word "density" and the phrase "specific gravity" as used in this specification and/or claims are directly proportional to one another and are clearly equivalent.

The change of viscosity and/or density of the contents of pipeline 10 from the location of $p_a$ to the location of $p_d$ along the length of the pipeline 10 is assumed insignificant in net oil computer and other applications.

In FIG. 2, wiper 35 may be above electrical ground and wiper 36 may be below electrical ground. The adder 37 thus adds the potentials of wipers 35 and 36. This, of course, can be done other ways. For example, if the potentials of wipers 35 and 36 are both positive or both negative, the ground of 43 may be removed and resistor 48 reconnected from wiper 36 to the noninverting input of amplifier 42.

What is claimed is:

1. A densitometer comprising: a piperline having a vertical portion and a horizontal portion; first means for producing a first electrical output signal proportional to the difference between the pressures at two different respective elevations in said vertical portion; second means for producing a second electrical output signal proportional to the difference between the pressures at two different respective locations along the length of said horizontal portion inside thereof; third means for producing a third electrical output signal proportional to the difference between the magnitudes of said first and second electrical output signals, said third means including an electrical analog adder-subtractor; and utilization means connected to receive said third electrical output signal.

2. The invention as defined in claim 1, wherein said utilization means includes a voltmeter calibrated in density or specific gravity.

3. The invention as defined in claim 2, wherein said pipeline has the same uniform inside diameter along the said vertical and horizontal portions thereof.

4. The invention as defined in claim 3, wherein said horizontal locations are at the same elevation.

5. The invention as defined in claim 4, wherein said elevations in said vertical portion are spaced apart a distance $L_a$ and said two locations are spaced apart a distance $L_b$, said distance $L_a$ being equal to said distance $L_b$.

6. The invention as defined in claim 1, wherein said pipeline has the same uniform inside diameter along the said vertical and horizontal portions thereof.

7. The invention as defined in claim 6, wherein said horizontal locations are at the same elevation.

8. The invention as defined in claim 6, wherein said elevations in said vertical portion are spaced apart a distance $L_a$ and said two locations are spaced apart a distance $L_b$, said distance $L_a$ being equal to said distance $L_b$.

9. The invention as defined in claim 8, wherein said utilization means includes a voltmeter calibrated in density or specific gravity.

10. The invention as defined in claim 1, wherein said horizontal locations are at the same elevation.

11. The invention as defined in claim 10, wherein said utilization means includes a voltmeter calibrated in density or specific gravity.

12. The invention as defined in claim 1, wherein said elevations in said vertical portion are spaced apart a distance $L_a$ and said two locations are spaced apart a distance $L_b$, said distance $L_a$ being equal to said distance $L_b$.

13. The invention as defined in claim 12, wherein said utilization means includes a voltmeter calibrated in density or specific gravity.

* * * * *

UNITED STATES PATENT OFFICE
CERTIFICATE OF CORRECTION

PATENT NO. : 4,417,474

DATED : November 29, 1983

INVENTOR(S) : P. Elderton

It is certified that error appears in the above-identified patent and that said Letters Patent are hereby corrected as shown below:

"Assignee: ITT" should be changed to

---Assignee: International Telephone and Telegraph Corporation---

Signed and Sealed this

Twenty-seventh Day of March 1984

[SEAL]

Attest:

GERALD J. MOSSINGHOFF

Attesting Officer

Commissioner of Patents and Trademarks